United States Patent [19]
Falkenhagen et al.

[11] Patent Number: 5,855,782
[45] Date of Patent: Jan. 5, 1999

[54] ARRANGEMENT FOR REMOVING SUBSTANCES FROM LIQUIDS, IN PARTICULAR BLOOD

[76] Inventors: Dieter Falkenhagen, Stockerauer Str. 52, A-2104 Spillern; Heinrich Schima, Kornergasse 7/9, A-1020 Vienna, both of Austria; Fritz Loth, Mahlower Str. 211, 14513 Teltow, Germany

[21] Appl. No.: 596,089
[22] PCT Filed: Aug. 10, 1994
[86] PCT No.: PCT/EP94/02644
§ 371 Date: Feb. 9, 1996
§ 102(e) Date: Feb. 9, 1996
[87] PCT Pub. No.: WO95/04559
PCT Pub. Date: Feb. 16, 1995

[30] Foreign Application Priority Data
Aug. 10, 1993 [AT] Austria ............... A 1599/93
[51] Int. Cl.⁶ ............ B01D 61/00; B01D 65/10; B01D 15/00
[52] U.S. Cl. ............ 210/323.1; 210/85; 210/195.2; 210/201; 210/223; 210/252; 210/258; 210/321.6; 210/321.65
[58] Field of Search ............ 210/85, 90, 97, 210/103, 117, 137, 195.2, 201, 198.1, 222, 223, 252, 258, 257.2, 323.1, 321.6, 321.65, 321.78, 321.79, 321.8, 433.1; 604/4, 5, 6

[56] References Cited
U.S. PATENT DOCUMENTS

| | | | |
|---|---|---|---|
| 3,619,423 | 11/1971 | Galletti et al. | 210/195.2 |
| 3,963,613 | 6/1976 | Chibata et al. | 210/195.2 |
| 3,979,284 | 9/1976 | Granger et al. | 210/321.65 |
| 4,024,059 | 5/1977 | Sausse | 210/195.2 |
| 4,118,314 | 10/1978 | Yoshida | 210/321.6 |
| 4,178,240 | 12/1979 | Pinkerton | 210/646 |
| 4,366,061 | 12/1982 | Papanek et al. | 210/647 |
| 4,474,690 | 10/1984 | Nylen | 210/651 |
| 4,813,924 | 3/1989 | Strahilevitz | 210/651 |
| 5,078,885 | 1/1992 | Matsumura | 210/321.72 |
| 5,211,850 | 5/1993 | Shettigar et al. | 210/195.2 |
| 5,277,820 | 1/1994 | Ash | 210/195.2 |
| 5,476,444 | 12/1995 | Keeling et al. | 604/4 |
| 5,536,412 | 7/1996 | Ash | 210/646 |

FOREIGN PATENT DOCUMENTS

| | | |
|---|---|---|
| 0143178 | 6/1985 | European Pat. Off. |
| 2472936 | 7/1981 | France |
| 4113602 | 10/1992 | Germany |

*Primary Examiner*—John Kim
*Attorney, Agent, or Firm*—Omri M. Behr, Esq.

[57] ABSTRACT

The present invention is directed to an arrangement for the elimination of substances by means of a membrane filter wherein the use is foreseen both in the blood cleaning procedures as well as in chemical and biotechnological separation techniques. The fluid containing the substances is run through the primary side of the membrane filter and the secondary side is flowed through by a adsorptive suspension which contains the substance binding particles. A pump drives the adsorptive suspension through the secondary side of membrane filter and causes in this way locally differentiable positive and negative transmembrane pressure differences whereby a local fluid exchange occurs and by means of which the active substances come into contact with the particles. Since the volume of the adsorptive suspension in the secondary circuit is held constant, the mean transmembrane pressure does not alter.

42 Claims, 8 Drawing Sheets

ARRANGEMENT FOR REMOVING SUBSTANCES FROM LIQUIDS, IN PARTICULAR BLOOD

This application is a 371 of PCT/EP94/02644 filed 8/10/94.

FIELD OF THE INVENTION

Arrangement for the elimination of substances from fluids

BACKGROUND OF THE INVENTION

The invention is directed to an arrangement for the elimination of substances from fluids in particular blood which comprises in the first circuit wherein the fluid to be treated flows, an attachable membrane filter and in whose secondary, for example, filtrate side there is a suspension containing an adsorbent for binding those substances passing through the membrane.

The elimination of patho-physiologically relevant substances can be carried out with extra corporeal systems, wherein membrane filters and adsorption procedures may be utilized. Included in such processes there may particularly be mentioned hemodialysis, high-flux hemodialysis, hemofiltration, membrane plasma separation, hemoperfusion and plasma perfusion. For special purposes, for example, the therapy of liver failure, hybrid systems which comprise the provision of special cell types such as hepatocytes, are in clinical trial. For example, such therapeutic procedures are utilized for chronic kidney insufficiency, acute exogenic intoxication, acute and chronic liver insufficiency, endotoxin shock, metabolic disturbances, hyperlipidemia, and auto immune diseases. With respect to the presently known pathophysiologically relevant substances, one is concerned with a substantial spectrum of different substances having different chemical (protein-lipid-waterbound, hydrophilic, hydrophobic) and different physical properties (molecular size, molecular weight) for which reason different procedures must be utilized.

DISCUSSION OF THE PRIOR ART

In order to eliminate substances such as LDL-cholesterol, endotoxins, antibodies, antigens, and protein/lipid bound materials in a selective manner, it is preferred to utilize adsorption protected procedures. The disadvantages of such systems is as follows:

The difficulty of applying a system which guaranties blood contact because of the problem of blood compatibility, in particular where finely divided adsorbents are concerned.

With plasma perfusion as is illustrated in FIG. 1, a filtrate is pumped out from filter (1) through exit (6) into the secondary circuit (12) by pump (13). The filtered plasma then flows through a capsule (41) which contains particles binding the effective material. Then the cleaned plasma flows back to the patient 31 through primary circuit (11). This procedure is very costly economically and technologically. Because of the limited binding capacity of particles in capsule (41), it is necessary to regenerate or flop them out during the use under clinical conditions.

While it is desirable to utilize the smallest possible particles since these give rise to the largest surface area, however, the use of such smaller particles in capsule (41) leads to higher packing densities and thus to higher flow resistance which give rise to a very substantial pressure drop between input (42) and output (43).

Furthermore, because of the plasma removal in filter (1), there is a thickening of the blood in vicinity of the exit of the membrane filter which gives rise to risks of blood clot formation.

Because a mechanically reliable binding of the particles in capsule (41) cannot be absolutely guarantied, for safety reasons a further filter is provided before input into the patient through input (9).

Where there are utilized suspensions containing adsorptive material in the known procedures (for example, biologic DT, PCT WO93/15825 Ash and U.S. Pat. No. 5,078,885, Matsomura) reliance is principally made on the known principles of diffusion. Therein there are either utilized selective procedures such as the use of asymmetrically constructed membranes in combination with the correspondingly formed and therefore very expensive adsorbent particles or the use of expensive pumping systems to obtain the pulsing forwarding and turn over of the suspension. Thus, both procedures are associated with high costs.

An arrangement for the elimination of substances set comprising a first and a second fluid circuit having at least one membrane filter therebetween capable of allowing passage therethrough of the substances to be eliminated, said membrane having a primary side in said first circuit and a secondary side in said second circuit, said fluid to be purified being located in said first circuit and said second circuit comprising an adsorbent containing suspension of particles for binding said substances to be eliminated, a first pump located in said first circuit for circulation of the fluid to be purified, and a second pump located in said second circuit for circulation of the adsorbent containing suspension, is known from U.S. Pat. No. 3,963,613. The known arrangement permits the removal of selective substances by the use of dialysate by means of different enzymes, which are present in the suspension or may be encapsulated. In a preferred embodiment, the known arrangement utilizes two dialysers switched in parallel, wherein one chamber of the second dialyzer is not connected in a fluid circuit.

The known arrangement is directed solely to the diffusive elimination of a low molecular substances.

EPAO 143178 describes an arrangement for blood purification with a filter whose primary compartment is switched into the blood circuit and whose secondary compartment is switched into a secondary circuit into which an adsorption capsule is connected. An adsorbent containing suspension is not present in the second circuit. The achievement of locally differing positive and negative transmembrane pressure results solely from raising of the flow rate of blood in the primary circuit.

SUMMARY OF THE INVENTION

The purpose of the present invention is to provide an arrangement of the type mentioned in the prior art, wherein substances may be removed from the fluid in particular from blood with a higher sale activity and higher adsorptive efficiency, this particular problem is solved by providing that the second pump is drivable at a forwarding speed so that there is a passage of the substance containing fluid across the membrane filter between said first and second circuits, said pump in said second circuit being a means for achieving regionally occurring differentiable positive and negative transmembrane pressure on said membrane.

In the arrangement in accordance with the present invention the medium, in particular blood, containing the substance to be eliminated is led through a membrane filter in particular a plasma filter or a hemofilter which is divided on the one side into a blood chamber and on the other side into a filtrate chamber. Herein the blood chamber is the primary side to which, in the conventional manner, blood is led via a first pump, suitably a peristaltic pump.

The filtrate chamber which comprises the secondary side, that is to say the filtrate side, is loaded with a cleaning suspension which contains particles which are enabled to bind the substance to be removed. This fluid as is conventional further comprises an electrolyte having isotonic composition.

Thus, the cleaning suspension is run through the filtrate chamber of the membrane filter at forwarding speed by means of a second pump which is provided in the secondary circuit.

Furthermore, it is important with respect to the present invention that there is a means for obtaining different positive and negative transmembrane pressures at different areas of the membrane. This is most readily carried out with the so-called high-flux membranes which are commercially available in many different forms. These characterize themselves by a high water permeability in dependence on the surface area of the membrane, the pressure, and the treatment time. Such high-flux membrane filters, at room temperature, have a permeability for water of the order of 15 to 20 mm per hour X $m^2$×mm and more.

By reason of the flow conditions of the cleaning suspension on the outer side of the filter membrane, conventionally constructed from hollow fibers, there occurs a pressure drop between the inflow side and the outflow side of the filtrate chamber which has the consequence that at a sufficiently high input pressure which is substantially determined by the flow speed and the flow resistance of a medium in the filtrate chamber, fluid may be forced through the pores of the membrane into the blood path.

Generally speaking, the secondary volume is constant which has the consequence that on the opposite side the same conditions occur in reverse sequence, that is to say, that a back filtration occurs of the fluid volume previously passed through the membrane. It is advantageous if the membrane filter is run in a counter-current fashion, that is to say, the two fluids flow through each chamber in opposite directions. Thus, at the input of the chamber, there is a positive pressure, which is correlated at the output of the chamber with a negative pressure. During the cleaning of blood, this has the consequence that blood plasma together with the substances to be eliminated on the blood input side, move through the membrane to the filtrate side where they are freed from the substance to be removed and again returned to the opposite side because of the balancing of the blood circuit.

It is furthermore important to the present invention that the volume of the secondary circuit is held in balance which conventionally occurs by holding the volume of the secondary circuit constant.

It is advantageous that the pump in the secondary circuit is combined with a means for obtaining a different transmembrane pressure which occurs because the pump is driven with the appropriate input pressure to relatively high through-put rates of 0.5 to 6, suitably 1–3 liters/min.

It is further advantageous to provide that the pump utilized for forwarding the suspension in the secondary circuit is a centrifugal pump which is characterized by a low mechanical shear loading with respect to the suspended adsorption particles. Thus, there occurs a very minimal mechanical damage of these particles during the pumping process.

In a further advantageous embodiment, there is provided, in addition to the first membrane filter, a second membrane filter in series with the first membrane filter so that both blood chambers and filtrate chambers are sequentially flowed through by blood and cleaning suspension. This arrangement leads to an increase in elimination efficiency since an adjustable clamp is provided in the connection line between the filters on the filtrate side, as a further means for achieving different transmembrane pressures.

As previously mentioned, the secondary circuit is provided with a balancing arrangement wherein the amounts of fluid lead in and lead out may be balanced. Such a balancing arrangement can be provided by two similarly driven forwarding arrangements (pumps), wherein one is provided to the input branch and the other to the output branch of the circuit. This pumping arrangement (for example a double hose pump) can input and output identical amounts of cleaning suspension. On the other hand, a balancing chamber system may also be utilized as it is described, for example, in German patent DE 28 38 414 and is utilized in many balanced hemodialysis arrangements.

It is preferred that the cleaning suspension is only run through the secondary circuit until its elimination capacity is almost exhausted. Furthermore, it is desirable that the exhausted cleaning suspension is, if possible, not mixed with fresh cleaning suspension, which may be advantageously achieved by means of a blocking valve which prevents such mixing. Furthermore, a pump may be provided to accelerate this exchange.

A plurality of components coming into contact with biological fluids in particular blood, are formed for but a single utilization (so-called disposables) wherein, for example, the pump utilized in the secondary circuit is comprised of a replaceable drive portion and a single use pump head.

Furthermore, the arrangement of the present invention advantageously comprises detectors for recognition of defects in the filters which are manifested in the fluid of the primary circuit. Included in such detectors are ultrasound detectors, photo-optical sensors which can report photo-optically detectable substances, magnetic sensors which can report magnetically active materials and the like.

In accordance with another embodiment a fabric filter is provided after the output of the membrane filters so that in the event of a defect permitting the passage of adsorption particles, these are detected and held back before their entry into the blood path of a patient.

Furthermore, after the output of the primary side of the membrane filter, there may be provided a magnetic field which can deflect magnetically active materials which present as particles in the cleaning suspension, whereas these particles arrive in the primary side due to a defect in the membrane filter.

It is furthermore advantageous if pressure sensors are provided to the input and output sides of the chambers of the membrane filters so that the transmembrane pressure may be reported over the entire membrane and thus the two pump levels which are the means for achieving different membrane pressures can also be controlled in a predetermined manner.

The particles provided in the cleaning suspension are selected with reference to the substance to be eliminated. Thus, for example the arrangement of the present invention is particularly suitable for the removal of endotoxins or other mediators including cytokines such as the Tumor-Necrose factor or Interleukin 1. The particles thus have a very high adsorption capacity which is characterized by a surface covered with large amounts of the substances. It is particularly advantageous to use the so-called microspheres which generally have a diameter of between 5 and 50 $\mu$m.

If it is desired to remove endotoxins from plasma, one has to ensure that these, by virtue of their phosphate groups are loaded in physiological media (blood pH 7.36–7.44). Therefore, adsorber matrices containing cationic substances should be used. Cellulose beads are particularly advantageous when they are modified with cationic substances, for example with diethylaminoethyl groups or with polyethylene imine groups.

In a totally different clinical area, for example, the therapy of hyperlipid-demia, the technology of the present invention may be utilized for LDL adsorption. Also here, cellulose beads, suitably with a diameter of 5 $\mu$m may be utilized.

There may also be used natural cells such as fibroblasts or the like which show no metabolic or morphological damage after 5 hours of running through secondary circuit.

It has been determined that for the success of the arrangement of the present invention, it is only necessary that the cleaning suspension is pumped through the secondary chamber of the membrane filter in a balanced manner, that is to say, with such an input pressure that on one side of the filter, filtered cleaning suspension is lead over into the blood chamber and on the other side, the same volume of plasma is transported onto the filter side.

BRIEF DESCRIPTION OF THE DRAWINGS

The drawing illustrates the invention in connection with the following working examples.

They show.

DESCRIPTION OF THE PREFERRED EMBODIMENTS

Figure 2:
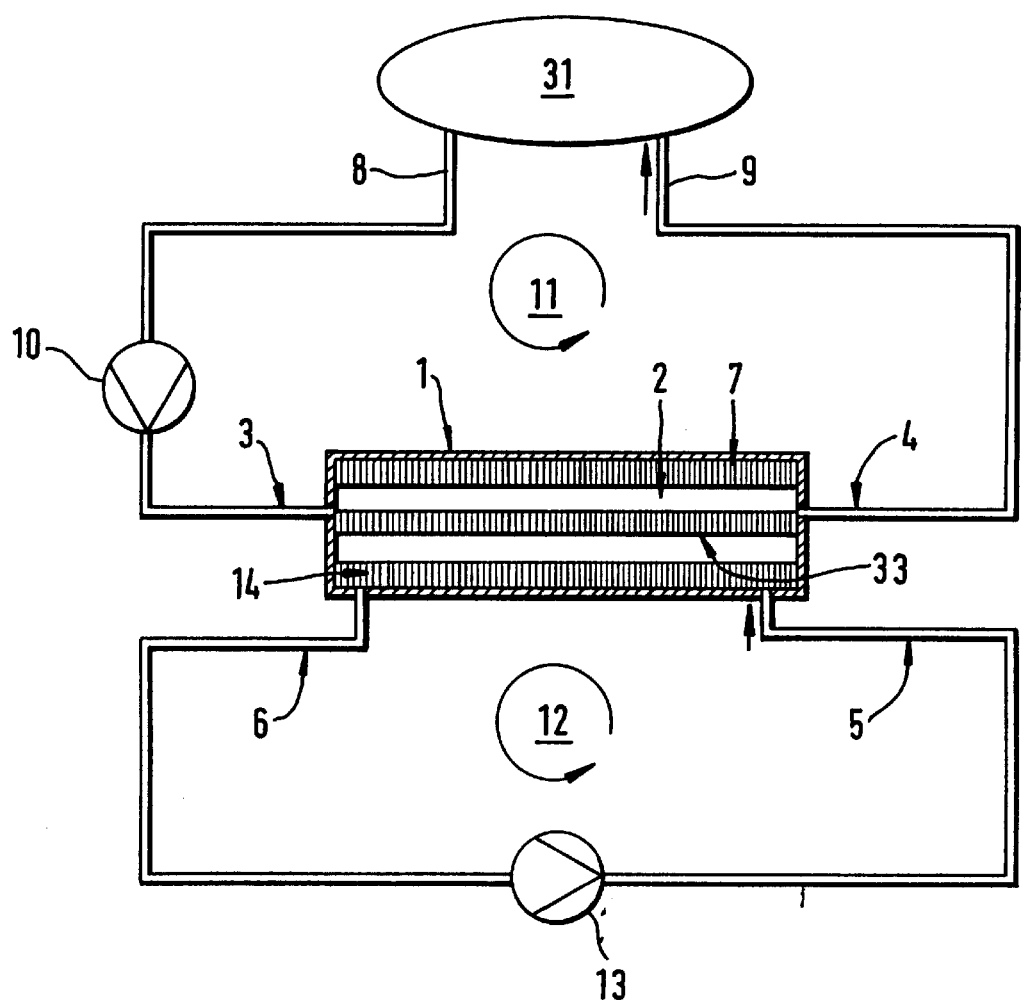
FIG. 2—A first embodiment of an arrangement in accordance with the present invention for the elimination of substances from blood.

FIG. 2 shows the principle elements of the invention; the primary circuit (11) of the arrangement guides venous or arterially sourced blood of patient 31, that is to say, the fluid to be cleaned, via a hose (8) to the input (3) of the primary side (2) of the membrane filter (1) and further from output (4) of the membrane filter (1) over the hose (9) back to the patient or recipient. In order to maintain or increase the flow in the primary circuit, there may be provided a pump (10). The secondary circuit (12) of the arrangement is filled with a cleaning suspension which comprises the particles binding the active substance wherein the carrier fluid in the suspension can have active effects and can further comprise active substances in the known manner such as, for example, albumin. The cleaning suspension is driven by a pump (13) through the secondary circuit (12) wherein this pump may not damage the particles (14) mechanically, thermally or chemically. A pump should be utilized which has minimal shearing effect. This may be particularly obtained with a centrifugal pump. The pump moves the cleaning suspension through input (5) of the secondary side (7) of membrane filter (1), whereby the cleaning suspension exits through exit (6). Because of the flow and current resistance of the membrane filter, pressure differences arise between input (3) and output (4) on the primary side (2) as well as between input (5) and output (6) on the secondary side. There thus arises locally differentiable transmembrane pressure differences between the primary and secondary side in the vicinity of the primary input (3) and the secondary output (6) between the primary side and secondary side (designated as positive) and in the vicinity of the secondary input (5) and the primary input (4) between the secondary side and the primary side (designated as negative). This leads to an exchange of fluid containing active substances moving through the filter membrane (33) between the primary and secondary side. Where the circulating volume of the cleaning suspension of the secondary circuit (11) is held constant, in the stationary condition there can be no permanent volume shift since, for example, an excessive transfer of fluid onto the primary side (2) would lead to an under pressure on the secondary side (7) and thus again to an overflow of fluid onto the secondary side (7). This has the consequence that in maintaining the volume of the secondary circuit (12) constant, the mean transmembrane pressure must be zero.

At the same time, the local transmembrane pressure differences will rise, both through a rise in the flow of the primary circuit (11), as well as through the rise of the flow in the secondary circuit (12), which increases the flow exchange and thus the elimination rate. The desired local pressure gradients to an effective filtration for medical purposes lie 1 and 20 kPa. In utilization in chemical and biotechnical separation techniques, even higher local pressure gradients may be provided. Instead of the countercurrent principle illustrated in FIG. 2, in which the flows on the primary and secondary side are opposed to each other, one may also utilize the costreaming principle with flows running in the same direction.

By achievement of these local different pressures gradients, the present invention is basically distinguishable from the known devices (for example Biologic DT) in which a suspension is circulated at a rate insufficient to achieve such gradients.

Figure 3:
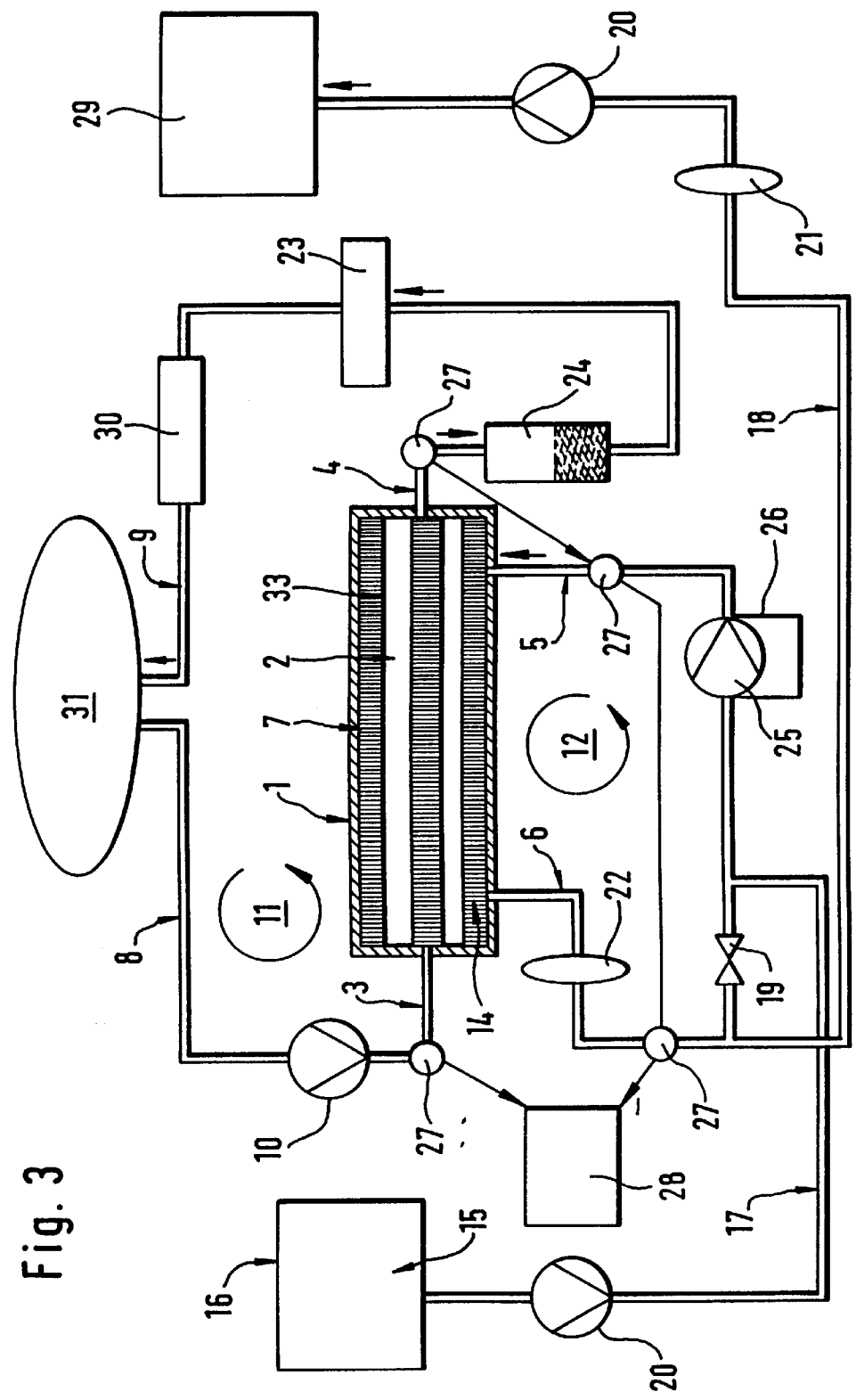
FIG. 3—A second embodiment of an arrangement in accordance with the present invention set forth in schematic format.

FIG. 3 illustrates an arrangement with possible expansions for the improvement of efficiency and security.

For replacing the cleaning suspension saturated with the active substance there may be provided an arrangement wherein the cleaning suspension is either renewed continuously with a evenly running pumping systems or discontinuously. In order to maintain the volume of the secondary circuit (12) as constant, there may be provided a double-hose pump (20) or another pump system with two similar forwarding arrangements, which pump the new cleaning suspension from reservoir (16) and a conduit (17) into the secondary circuit (12) and from these, the previously utilized cleaning suspension through exit (18) leads the used-up cleaning suspension into reservoir (29). In place of the double-hose pump, there may be utilized an arrangement of valves in input (17) and exit (18) wherein additionally there may be provided a single pump for accelerating the exchange. In order to reduce the mixing of old and new cleaning suspensions, there may additionally be provided a blocking valve (19) which prevents the recirculation in secondary circuit (12) during the discontinuously effected exchange. Furthermore, for the improvement of the exactness of the balancing, there may be provided conventionally known arrangements such as weight and volume measuring devices or balancing chambers for the input and output pumping with the same forwarding volume.

In order to avoid contamination of the arrangement during clinical use by re-use and to avoid subsequent damage to patient 31 all parts in contact with the blood or in contact with the cleaning solution are generally speaking single use articles, which are only used once. This is achieved in the pump by division into a single use pump head (25) and a reusable drive (26) which are magnetically coupled in a conventional manner or which are connected to each other by an insulated shaft.

In order to ensure the security of the patient in the event of failure of membrane filter (1) for example by a rupture of the membrane, it is at a minimum necessary to avoid the entry of particles (14) into the blood circuit and thus into the primary circuit (11) or at least detect them. Where the particles (14) are substantially bigger than the blood components, this can be achieved in a conventional manner by a fabric filter (24) which prevent the entry of particles (14) into patient 31. Where the particles (14) are of a similar size or order of magnitude as the blood components, a detector (23) should be provided into the primary circuit in order to close down the arrangement. This detector can be provided for the recognition of inhomogeneities in the blood by ultrasound or may be photo-optically sensitive wherein the cleaning suspension is colored with a material recognizable by the detector (coloring materials which absorb in the visible or not visible spectrum, luminescent, fluorescent or phosphorescent materials). A further possibility for the filtration removal of particles (14) exists in the provision of a magnetic field in utilization of magnet activatable parts of particles (14). The magnetic field drives the particles (14) which intrude into primary circuit (11) into a trapping arrangement (30) where they are held. Such a trapping arrangement may also be provided in the secondary circuit.

Furthermore, a conventional detector (22) may be provided in the secondary circuit (12) for the recognition of erythrocytes and/or free hemoglobin. The presence of erythrocytes in the secondary circuit would signal a membrane rupture while free hemoglobin signals the destruction of erythrocytes, for example because of excessively high pressure differences. In order to avoid high pressure differences, pressure sensors (27) may be provided in the entry and/or exit lines (3,4,5,6) of membrane filter (1). These can be coupled to signal devices which would advise the user with respect to setting the pumping speeds and with respect to the condition of the membrane filter (for example, the filtration arrangement) and other parts of the arrangement. This setting of the pumping speed can also be provided with an automatic control arrangement (28) for the assistance of the user.

In order to avoid an uneven distribution of particles in the cleaning suspension and in particular in reservoir (16), there may be provided a vibration or rocking arrangement.

For particular purposes, for example the replacement of eliminated substances by therapeutically indicated substances such as albumin, the cleaning suspension may be loaded with such therapeutical substances. Furthermore, by a deliberately arranged imbalance between the input and output of the cleaning suspension in and from the secondary circuit (12), a fluid transfer into or out of patient 31 may be arranged when this appears necessary for volume substitution during blood loss or the reduction of edema.

Figure 4:
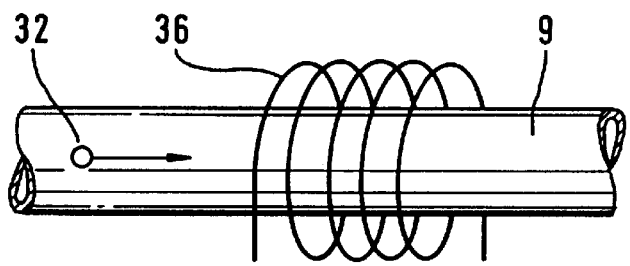
FIG. 4—The principle arrangement of a detector for the reporting of magnetically active particles.

In FIG. 4 an embodiment of detector (32) is illustrated in the form of a winding (36) around hose (9) in order to hold magnetically active particles. These particles induce a potential in winding (36) when they pass this.

In order to increase sensitivity the hose or the conduit may be lead through the detector (23) at a smaller diameter than the rest of the conduits of the primary side (11), whereby an improvement in the sensitivity is achieved by the higher flow rate.

Furthermore, the sensitivity may be improved and the security increased where a plurality of such windings (36) are sequentially placed around the hose, or next to hose (9) for the detection of perturbation fields.

Figure 5:
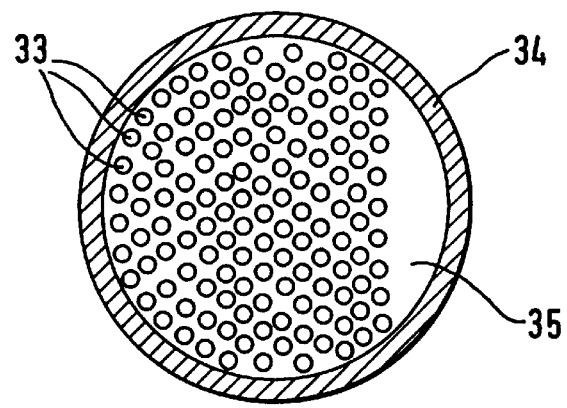
FIGS. 5 and 6—are cross sectional views of a hollow fiber membrane filter with the same distribution of hollow fibers inside the housing.
Figure 6:
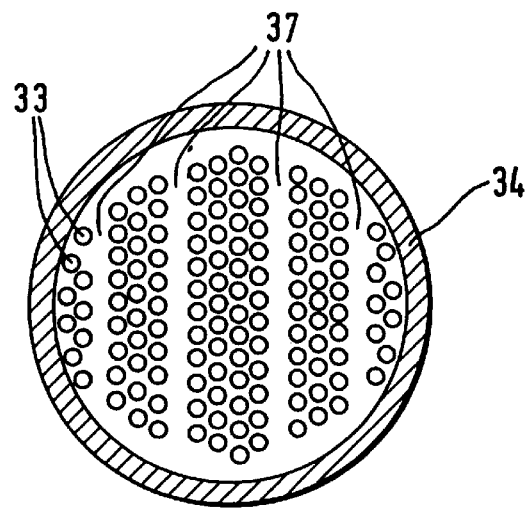

In FIGS. 5 and 6 embodiments of membrane filter (1) are shown in cross-section in which the membranes in the form of hollow fibers are distributed in an uneven manner over the inner surface of housing (34).

In accordance with FIG. 5, a channel (35) is provided which runs openly along the entire length of membrane filter (1) which allows for free passage of the cleaning suspension. Alternatively, in accordance with the illustration of FIG. 6, there is an embodiment showing a plurality of free channels (37) provided between the hollow fiber membranes (33).

Figure 1:
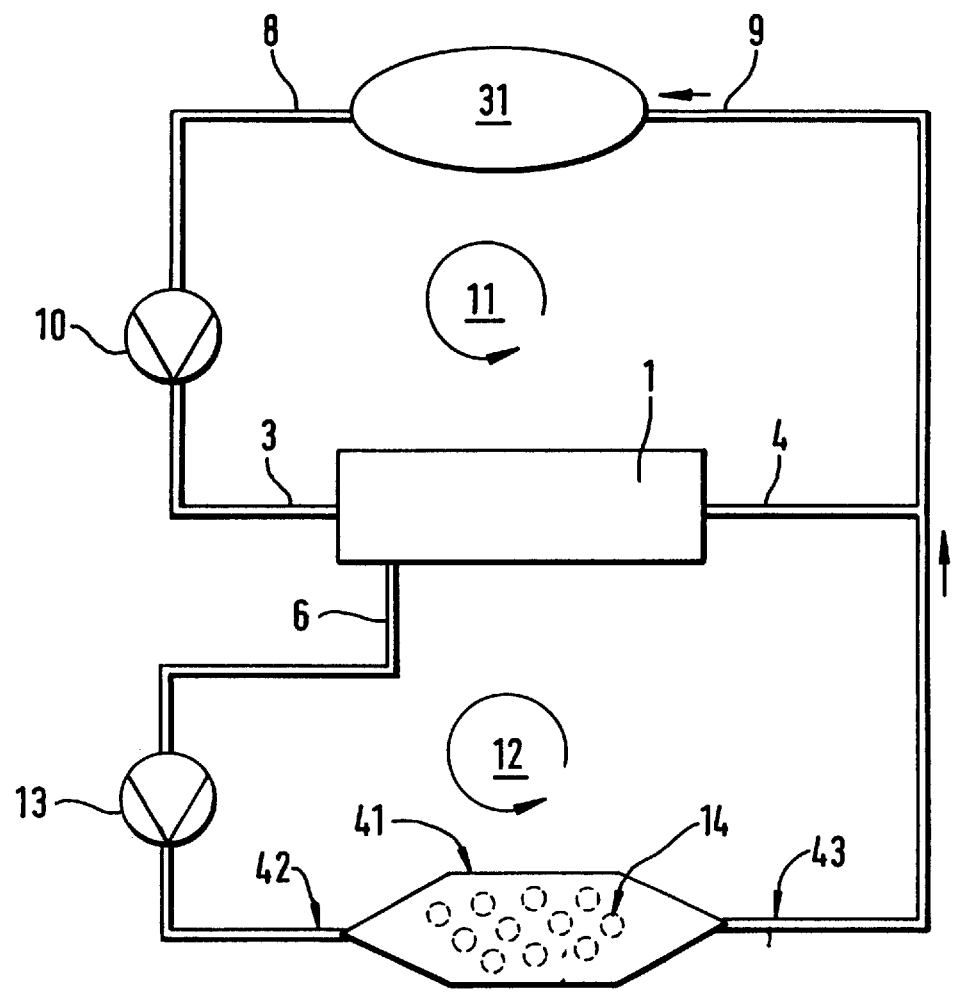
FIG. 1—A plasma perfusion arrangement.
Figure 7:
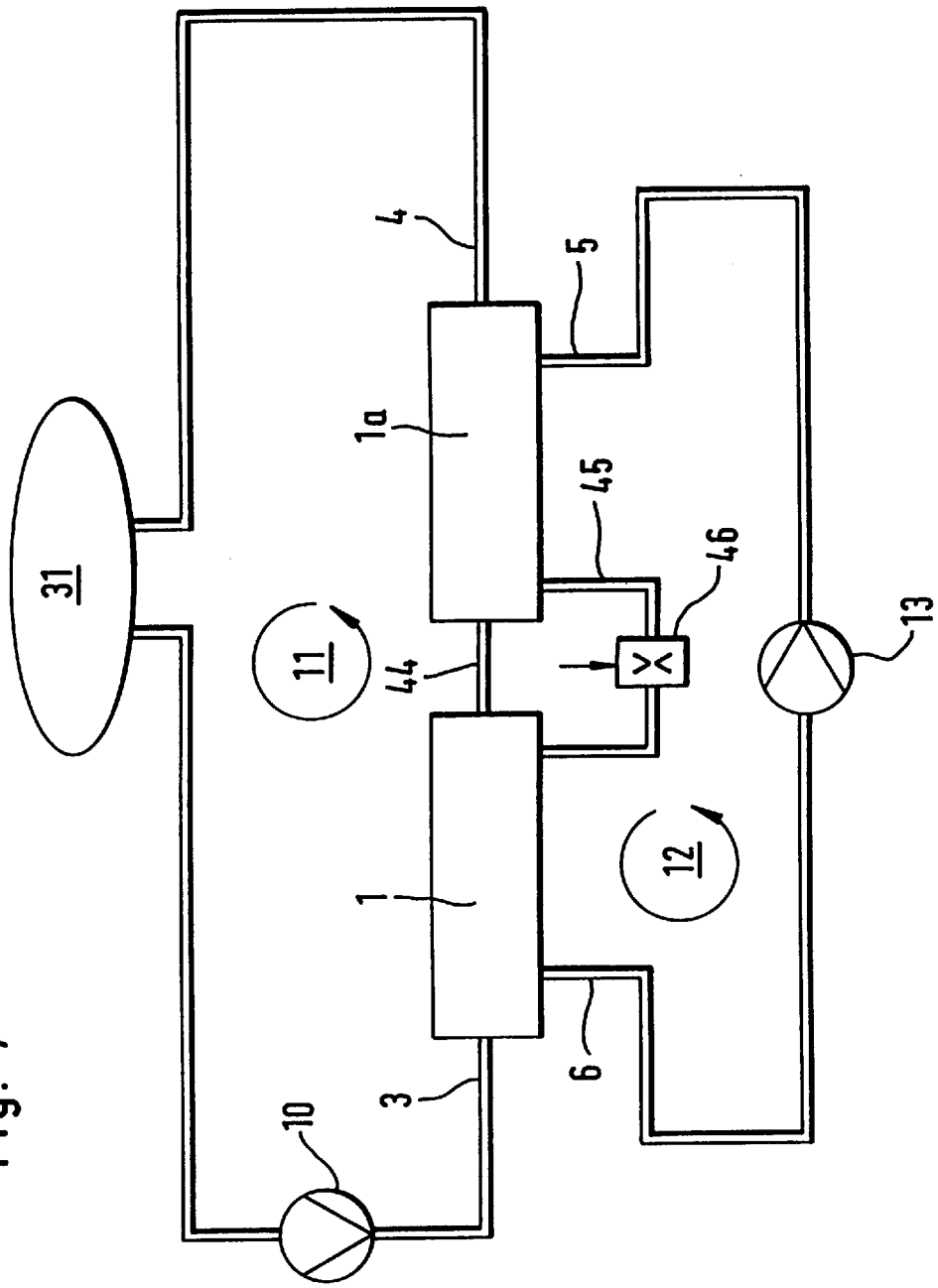
FIG. 7—A further embodiment of an arrangement of the present invention in schematic format showing two membrane filters.

A particularly preferred embodiment of the arrangement of the present invention is illustrated in FIG. 7 which may be differentiated from the embodiment of FIG. 1 only therein that instead of a single membrane filter (1) there are provided two membrane filters (1 and 1a) which are connected with each other by connection conduit (44) for the primary circuit and by connection conduit (45) for the secondary circuit. It is particularly advantageous to provide an adjustable clamp (46) in the latter combining circuit (45) as indicated by the arrow so that upstream of the clamp, a predetermined over-pressure may be provided which is correlated with corresponding under-pressure in the plasma filter (1) because of the balancing of the secondary circuit. This leads in membrane filter (1) in a predetermined manner to a transfer of a particular plasma volume into the secondary chamber where the elimination of the substance to be eliminated will occur. In the second membrane filter the same volume is lead back into the blood circuit (4). Because of the controllability of the clamp (46) therefore, one may preset the exact volumes to be handled.

One may further improve the system vis a vis the elimination efficiency of the single filter arrangement of FIG. 2 by the provision of two series provided filters (1 and 1a and 1b) in accordance with FIG. 7.

EXAMPLES 1 THROUGH 3

Example 1

In a batch experiment 18 ml of porcine plasma containing 2 ml of adsorbent are provided in a capillary plasma filter based on polypropylene (type P2 or P2S of the company Fresenius) with a membrane surface of 0.5 m$^2$. The secondary circuit comprises an endotoxin in the form of a lipopolysaccharide of Pseudomonas aeruginosa serotype 10 Habs in am amount of 20 mg/ml plasma. The total protein content is 4.3 g/dl plasma. It is incubated at 37° C.

Figure 8:
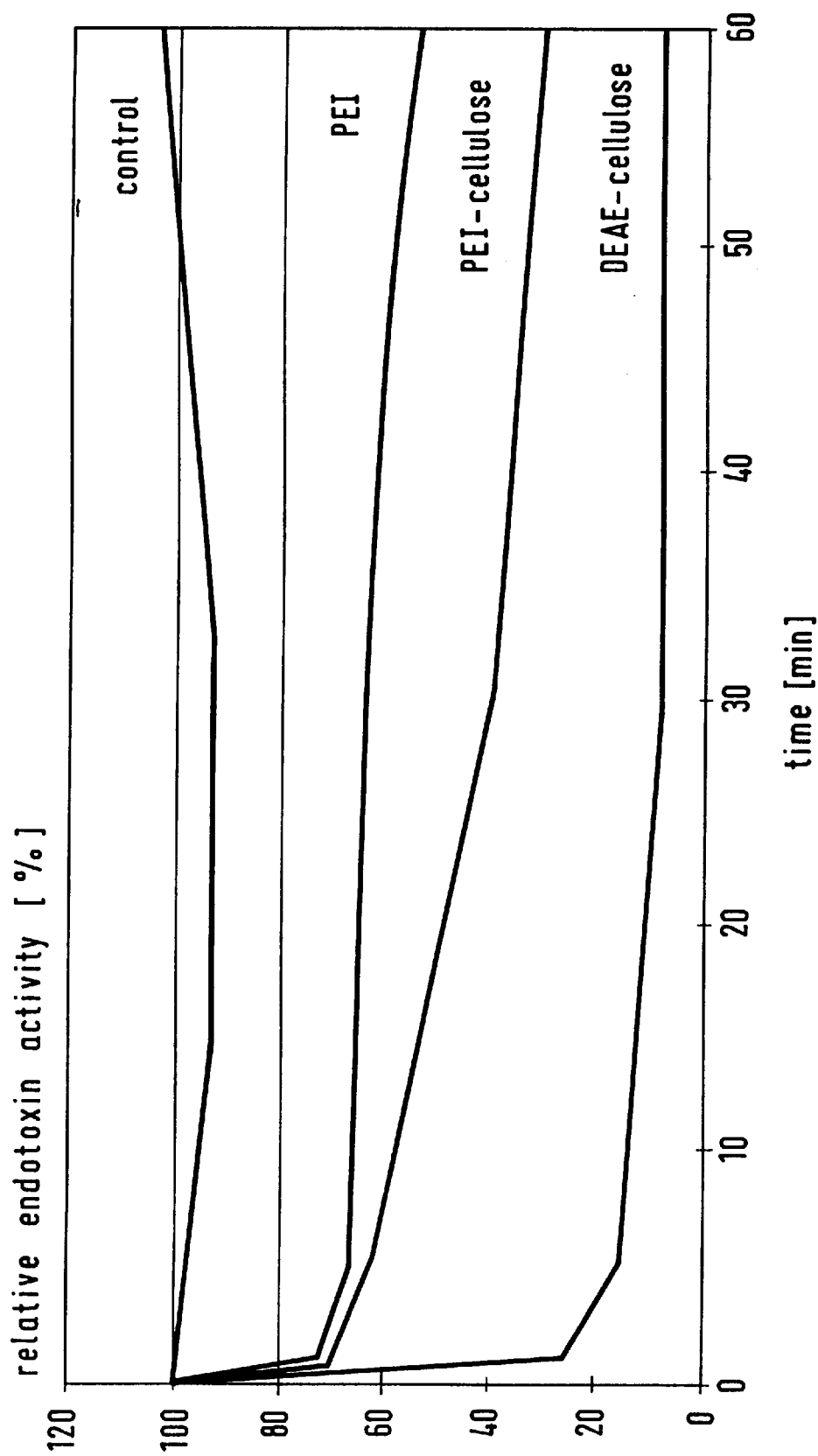
FIGS. 8 through 10—are curves of experiments utilizing the arrangement of the present invention wherein the ordinates show the amounts of substance to be removed and the abscissae show the time taken.

FIG. 8 illustrates the relative endotoxin activity and percent against time wherein the upper line serves as control, that is to say, the secondary circuit contains no adsorption particles. The curves lying thereunder are directed to adsorption particles PEI (polyethyleneimine) as well as PEI cellulose (polyethyleneimine derivatized cellulose beads) and DEAE cellulose beads (diethylaminoethyl derivatized cellulose beads). The beads themselves (ca 10–20 µm) have a high adsorption capacity is due to the high level of coating on the surface of the particles.

From FIG. 8, it may be noted that the beads can eliminate at least half of the endotoxin amounts while DEAE cellulose removes more than 90% of the endotoxin within 10 minutes.

Example 2

Figure 9:
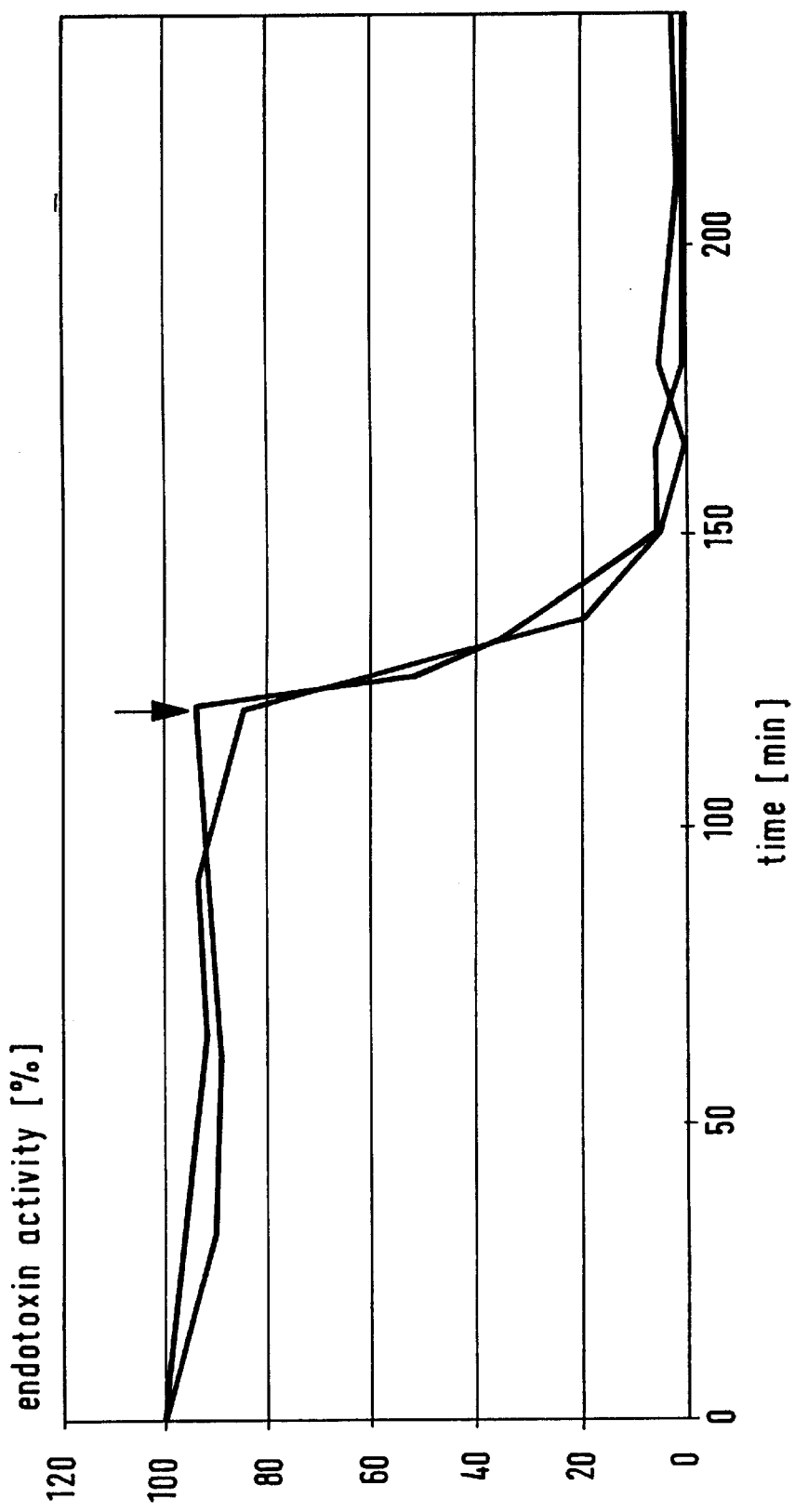

In FIG. 9 there is illustrated a similar endotoxin elimination wherein two filters corresponding to the embodiment of FIG. 7 are utilized. The total filter surface is 0.3 m² wherein hollow fiber membranes of polypropylene are utilized. 1.7 l of human plasma are provided to the primary side to which 40 mg/ml of endotoxin of Pseudomonas aeruginosa are added and incubated at 37° C. The full speed of the primary side runs at 0.2 l/min. and on the secondary side at 14 liters/min. To the secondary circuit, there are provided 90 ml. of modified PEI cellulose in 120 ml. of isotonic electrolyte solution.

The diagram illustrates that upon the addition of the micro beads (ca 5–10 mm diameter) the endotoxin concentration falls rapidly wherein this fall is illustrated in two tests. From this it may be seen that virtually all of the endotoxin is eliminated within half an hour.

Example 3

Figure 10:
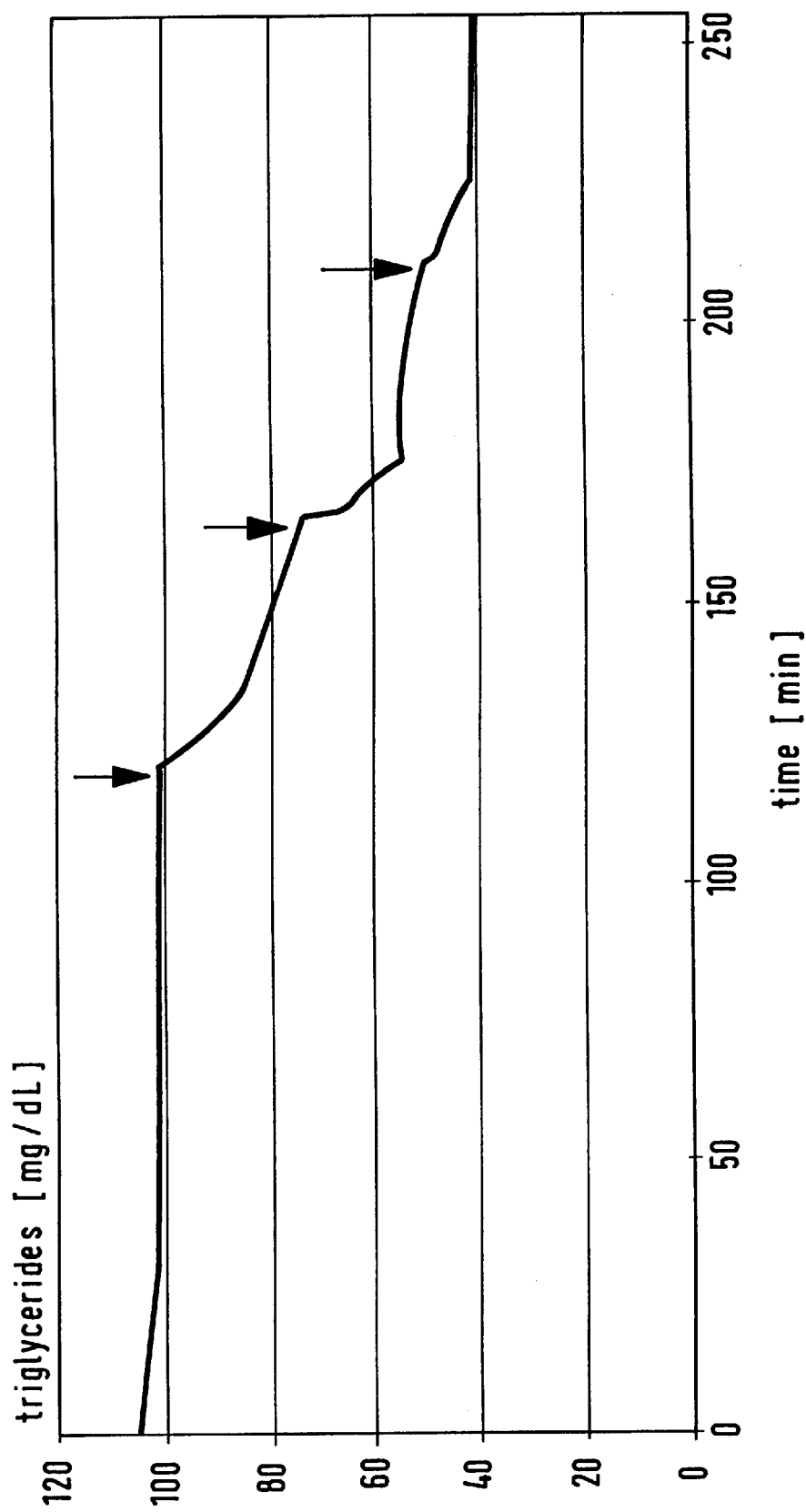

Example 3 shows another treatment process in accordance with the present invention wherein not only endotoxin but a plurality of other particles are removed by the choice of suitable adsorbents. In FIG. 10 there is illustrated the removal of triglycerides (LDL) in a two-filter version of FIG. 7. Again there are utilized polypropylene hollow fiber membranes with a total surface of 0.3 m². Into primary circuit there is pumped 1.7 liters of human plasma with a total protein content of 5 g/DL at 37° C. with a flow rate of 200 ml/min. The secondary side comprises an adsorbent for unmodified cellulose beads (R94/29) in isotonic electrolyte solution wherein the adsorbent is added in 140 ml portions at 120, 160 and 210 minutes (see the arrows in the Figure). The flow rate on the secondary side is 14 l/min. The secondary circuit contains 300 ml. of fluid. The LDL is determined by conventional methods.

From FIG. 10 it may be seen that the amount of triglycerides in the primary circuit is reduced in dependence upon the addition of adsorber beads.

We claim:

1. An arrangement for the elimination of substances from a fluid to be purified, comprising a first and a second fluid circuit having at least one membrane filter therebetween capable of allowing passage therethrough of the substances to be eliminated, said membrane filter having a primary side in said first circuit and a secondary side in said second circuit, said fluid to be purified being located in said first circuit and said second circuit comprising an adsorbent containing suspension of particles for binding said substances to be eliminated, a first pump located in said first circuit for circulation of the fluid to be purified, and a second pump located in said second circuit for circulation of the adsorbent containing suspension, wherein said second pump is drivable at a forwarding speed so that there is a passage of the substance containing fluid across said at least one membrane filter between said first and second circuits, said pump in said second circuit being a means for achieving regionally occurring differentiable positive and negative transmembrane pressure on said membrane filter of 1–20 kPa wherein two membrane filters are provided, the membrane of each filter having a primary side and a secondary side, the primary side of the first membrane filter and the primary side of the secondary membrane filter are connected in series by as first connection conduit and the secondary side of the first membrane filter and the secondary side of the second membrane filter are connected in series by a second connection conduit.

2. The arrangement according to claim 1 wherein the second pump directs the flow in countercurrent fashion relative to said first pump.

3. The arrangement according to claim 1 wherein the second pump has a forwarding capacity of between 0.5 to 6 l/min.

4. The arrangement according to claim 3 wherein the second pump has a forwarding capacity of between 1–3 l/min.

5. The arrangement according to claim 1 wherein said second pump is a centrifugal pump.

6. The arrangement according to claim 1 wherein all of the parts coming in contact with the adsorbent suspension are provided to be single use components.

7. The arrangement according to claim 6 wherein the pumps comprise a reusable drive and a single use pump head.

8. The arrangement in accordance with claim 1 wherein pressure sensors are provided at at least one of the inputs and outputs of the membrane filter.

9. The arrangement in accordance with claim 1 wherein the adsorbent suspension comprises active substances which are introducible into the second circuit by an exchange process, in addition to the particles for binding the relevant pathophysiological substances.

10. The arrangement accordance to claim 1 wherein there is provided a controllable clamp in said connection conduits.

11. The arrangement according to claim 1 wherein there is provided an inlet and outlet in said second fluid circuit, the inlet being in fluid communication with means for introducing fresh adsorbent suspension into said second fluid circuit and the outlet being in fluid communication with means for talking out therefrom an equal amount of used suspension for the exchange of used suspension with fresh suspension.

12. The arrangement according to claim 11 wherein the means for introducing fresh adsorbent suspension and taking out used suspension having pump means.

13. The arrangement according to claim 11 wherein the means for introducing fresh adsorbent suspension and taking out used suspension having valve means.

14. The arrangement according to claim 11 wherein there is provided a locking valve in said second fluid circuit between the inlet and outlet of said second circuit to prevent the mixing of the fresh and the used adsorbent suspension.

15. The arrangement according to claim 11 wherein there is provided a pump means in said second fluid circuit between the inlet and outlet of said second circuit for the acceleration of passage of fluid across the membrane.

16. The arrangement according to claim 11 wherein said means for introducing fresh adsorbent suspension into said second fluid circuit and said means for taking out therefrom an equal amount of used suspension comprises a control arrangement which enables different volumes of input and output of the adsorbent suspension into and from the second fluid circuit respectively.

17. The arrangement in accordance with claim 11 having a control arrangement which enables different volumes of input and output of the adsorbent suspension into and from the second fluid circuit.

18. An arrangement for the elimination of substances from a fluid to be purified, comprising
   a first and a second fluid circuit having at least one membrane filter therebetween capable of allowing passage therethrough of the substances to be eliminated, said membrane filter having a primary side in said first circuit and a secondary side in said second circuit,
   said fluid to be purified being located in said first circuit and
   said second circuit comprising an adsorbent containing suspension of particles for binding said substances to be eliminated,
   a first pump located in said first circuit for circulation of the fluid to be purified, and
   a second pump located in said second circuit for circulation of the adsorbent containing suspension,
   wherein said second pump is drivable at a forwarding speed so that there is a passage of the substance containing fluid across said at least one membrane filter between said first and second circuits, said pump in said second circuit being a means for achieving regionally occurring differentiable positive and negative transmembrane pressure on said membrane filter,
   wherein there is provided a detector located in said first circuit after the output of the primary side of the membrane filter, for noting defects in said filter, wherein the detector is an ultrasound filter which recognizes the presence of particles in the fluid of the first circuit.

19. An arrangement for the elimination of substances from a fluid to be purified, comprising
   a first and a second fluid circuit having at least one membrane filter therebetween capable of allowing passage therethrough of the substances to be eliminated, said membrane filter having a primary side in said first circuit and a secondary side in said second circuit,
   said fluid to be purified being located in said first circuit and
   said second circuit comprising an adsorbent containing suspension of particles for binding said substances to be eliminated,
   a first pump located in said first circuit for circulation of the fluid to be purified, and
   a second pump located in said second circuit for circulation of the adsorbent containing suspension,
   wherein said second pump is drivable at a forwarding speed so that there is a passage of the substance containing fluid across said at least one membrane filter between said first and second circuits, said pump in said second circuit being a means for achieving regionally occurring differentiable positive and negative transmembrane pressure on said membrane filter of 1–20 kPa wherein a fabric filter is provided after the output of the primary side of the membrane filter.

20. An arrangement for the elimination of substances from a fluid to be purified, comprising
   a first and a second fluid circuit having at least one membrane filter therebetween capable of allowing passage therethrough of the substances to be eliminated, said membrane filter having a primary side in said first circuit and a secondary side in said second circuit,
   said fluid to be purified being located in said first circuit and
   said second circuit comprising an adsorbent containing suspension of particles for binding said substances to be eliminated,
   a first pump located in said first circuit for circulation of the fluid to be purified, and
   a second pump located in said second circuit for circulation of the adsorbent containing suspension,
   wherein said second pump is drivable at a forwarding speed so that there is a passage of the substance containing fluid across said at least one membrane filter between said first and second circuits, said pump in said second circuit being a means for achieving regionally occurring differentiable positive and negative transmembrane pressure on said membrane filter,
   wherein there is provided a detector located in said first circuit after the output of the primary side of the membrane filter, for noting defects in said filter wherein, in the first circuit after the output of the primary side of the membrane filter, there is provided a magnetic field, and a trap arrangement,
   and wherein particles of the adsorbent suspension contain a magnetically active substance whereby, in the instance of a defect in the membrane filter, particles, which intrude into the primary side, are captured by said trap arrangement.

21. The arrangement according to claim 20 wherein the second pump runs in countercurrent fashion relative to said first pump.

22. The arrangement according to claim 20 wherein the second pump has a forwarding capacity of between 0.5 to 6 l/min.

23. The arrangement according to claim 20 wherein the second pump has a forwarding capacity of between 1–3 l/min.

24. The arrangement according to claim 20 wherein said second pump is a centrifugal pump.

25. The arrangement according to claim 20 wherein there is provided a third pump means having two equivalent forwarding arrangements which introduce into said second circuit and take out therefrom equal amounts of adsorbent suspension for the exchange of used suspension with fresh suspension.

26. The arrangement according to claim 25 wherein there is additionally provided a fourth pump for the acceleration of passage of fluid across the membrane and a locking valve to prevent the mixing of the used and the fresh adsorbent suspension.

27. The arrangement according to claim 20 wherein there is provided a valve arrangement for maintaining constant, volume in said second circuit.

28. The arrangement according to claim 27 wherein there is additionally provided a locking valve to prevent the mixing of used and fresh adsorbent suspension.

29. The arrangement according to claim 27 wherein there is additionally provided a fourth pump for the acceleration of passage of fluid across the membrane.

30. The arrangement according to claim 20 wherein all of the parts coming in contact with the adsorbent suspension are provided to be single use components.

31. The arrangement according to claim 30 wherein the pumps comprise a reusable drive and a single use pump head.

32. The arrangement in accordance with claim 20 wherein the regionally occurring differentiable positive and negative transmembrane pressure on said membrane filter of 1–20 kPa.

33. The arrangement in accordance with claim 20 wherein pressure sensors are provided at at least one of the inputs and outputs of the membrane.

34. The arrangement in accordance with claim 20 wherein the adsorbent suspension comprises active substances which are introducible into the second circuit by an exchange process, in addition to the particles for binding the relevant pathophysiological substances.

35. The arrangement according to claim 20 wherein there is provided an inlet and outlet in said second circuit, the inlet being in fluid communication with means for introducing fresh adsorbent suspension into said second fluid circuit and the outlet being in fluid communication with means for taking out therefrom an equal amount of used suspension for the exchange of used suspension with fresh suspension.

36. The arrangement according to claim 35 wherein the means for introducing fresh adsorbent suspension and taking out used suspension having pump means.

37. The arrangement according to claim 35 wherein the means for introducing fresh adsorbent suspension and taking out used suspension having valve means.

38. The arrangement according to claim 35 wherein there is provided a locking valve in said second fluid circuit between the inlet and outlet of said second fluid circuit to prevent the mixing of the fresh and the used adsorbent suspension.

39. The arrangement according to claim 35 wherein there is provided a pump means in said second fluid circuit between the inlet and outlet of said second fluid circuit for the acceleration of passage of fluid across the membrane.

40. An arrangement for the elimination of substances from a fluid to be purified, comprising a first and a second fluid circuit having at least one membrane filter therebetween capable of allowing passage therethrough of the substances to be eliminated, said membrane filter having a primary side in said first circuit and a secondary side in said second circuit, said fluid to be purified being located in said first circuit and said second circuit comprising an adsorbent containing suspension of particles for binding said substances to be eliminated, a first pump located in said first circuit for circulation of the fluid to be purified, and a second pump located in said second circuit for circulation of the adsorbent containing suspension, wherein said second pump is drivable at a forwarding speed so that there is a passage of the substance containing fluid across said at least one membrane filter between said first and second circuits, said pump in said second circuit being a means for achieving regionally occurring differentiable positive and negative transmembrane pressure on said membrane filter, wherein there is provided a detector located in said first circuit after the output of the primary side of the membrane filter, for noting defects in said filter wherein two membrane filters are provided, the membrane of each filter having a primary side and a secondary side, the primary side of the first membrane filter and the primary side of the secondary membrane filter are connected in series by as first connection conduit and the secondary side of the first membrane filter and the secondary side of the second membrane filter are connected in series by a second connection conduit.

41. The arrangement accordance to claim 40 wherein there is provided a controllable clamp in said connection conduit of said second circuit.

42. An arrangement for the elimination of substances from a fluid to be purified, comprising a first and a second fluid circuit having at least one membrane filter therebetween capable of allowing passage therethrough of the substances to be eliminated, said membrane filter having a primary side in said first circuit and a secondary side in said second circuit, said fluid to be purified being located in said first circuit and said second circuit comprising an adsorbent containing suspension of particles for binding said substances to be eliminated, a first pump located in said first circuit for circulation of the fluid to be purified, and a second pump located in said second circuit for circulation of the adsorbent containing suspension, wherein said second pump is drivable at a forwarding speed so that there is a passage of the substance containing fluid across said at least one membrane filter between said first and second circuits, said pump in said second circuit being a means for achieving regionally occurring differentiable positive and negative transmembrane pressure on said membrane filter, wherein there is provided a detector located in said first circuit after the output of the primary side of the membrane filter, for noting defects in said filter wherein a fabric filter is provided after the output of the primary side of the membrane filter.

* * * * *